(12) United States Patent (10) Patent No.: US 12,564,515 B2
Lörner et al. (45) Date of Patent: Mar. 3, 2026

(54) DOCKING AN EYE FOR OPHTHALMIC LASER TREATMENT

(71) Applicant: Alcon Inc., Fribourg (CH)

(72) Inventors: Johannes Lörner, Roßtal (DE); Peter Riedel, Nuremberg (DE); Stefan Schmid, Neuendettelsau (DE); Andreas Vetter, Erlangen (DE)

(73) Assignee: ALCON INC., Fribourg (CH)

( * ) Notice: Subject to any disclaimer, the term of this patent is extended or adjusted under 35 U.S.C. 154(b) by 348 days.

(21) Appl. No.: 18/301,130

(22) Filed: Apr. 14, 2023

(65) Prior Publication Data

US 2023/0338191 A1 Oct. 26, 2023

Related U.S. Application Data

(60) Provisional application No. 63/363,322, filed on Apr. 21, 2022.

(51) Int. Cl.
*A61F 9/008* (2006.01)
*G16H 20/40* (2018.01)

(52) U.S. Cl.
CPC ............. *A61F 9/008* (2013.01); *G16H 20/40* (2018.01); *A61F 2009/00846* (2013.01); *A61F 2009/00872* (2013.01)

(58) Field of Classification Search
None
See application file for complete search history.

(56) References Cited

U.S. PATENT DOCUMENTS

| | | | |
|---|---|---|---|
| 10,195,085 B2* | 2/2019 | Campos | ................. A61F 9/009 |
| 2013/0050649 A1* | 2/2013 | Juhasz | .................... A61F 9/008 |
| | | | 351/208 |
| 2015/0335479 A1 | 11/2015 | Shibata | |
| 2022/0062039 A1 | 3/2022 | Abraham et al. | |

FOREIGN PATENT DOCUMENTS

CA          3037296 A1     3/2018

OTHER PUBLICATIONS

Josephine Susai Christy, et al.; Learning curve of femtosecond laser-assisted cateract surgery: Experience of surgeons new to femtosecond laser platform; Indian Journal of Ophthalmology; published by Wolters Kluwer—Medknow; Aug. 2017; vol. 65 Issue 8; pp. 683-689.

* cited by examiner

*Primary Examiner* — Michael T. Holtzclaw

(57) ABSTRACT

An ophthalmic laser surgical system for treating an eye includes a laser device, one or more cameras, and a computer. The eye has anatomical features, including the cornea with the anterior corneal surface. The laser device directs a laser beam towards the eye. A camera generates images of the anatomical features, including the anterior corneal surface. The computer facilitates docking a patient interface onto the eye by accessing eye information describing the eye. The eye information comprises an eye model describing the anatomical features. The computer determines from the eye model the predicted corneal surface position when the eye is aligned to dock the patient interface onto the eye. The computer detects from the images the actual corneal surface position prior to docking the patient interface onto the eye, and compares the predicted corneal surface position with the actual corneal surface position to detect misalignment.

14 Claims, 3 Drawing Sheets

DOCKING AN EYE FOR OPHTHALMIC LASER TREATMENT

TECHNICAL FIELD

The present disclosure relates generally to ophthalmic laser systems, and more particularly to docking an eye for ophthalmic laser treatment.

BACKGROUND

In certain ophthalmic procedures, laser pulses are directed towards the eye to interact with, e.g., create photodisruptions, at specific locations of the eye. The pulses must land precisely at the specific locations of the eye, especially for procedures such as lenticular removal. Accordingly, a patient interface may be affixed to the eye (i.e., the eye may be "docked") to limit movement between the laser system and the eye and to create a reliable optical interface between the system and the cornea of the eye.

BRIEF SUMMARY

In certain embodiments, an ophthalmic laser surgical system for treating an eye includes a laser device, one or more cameras, and a computer. The eye has anatomical features, including the cornea with the anterior corneal surface. The laser device directs a laser beam towards the eye. A camera generates images of the anatomical features, including the anterior corneal surface. The computer facilitates docking a patient interface onto the eye by accessing eye information describing the eye. The eye information comprises an eye model describing the anatomical features of the eye. The computer determines from the eye model the predicted corneal surface position when the eye is aligned to dock the patient interface onto the eye. The computer detects from the images the actual corneal surface position prior to docking the patient interface onto the eye, and compares the predicted corneal surface position with the actual corneal surface position to detect misalignment.

Embodiments may include none, one, some, or all of the following features: The computer facilitates docking the patient interface onto the eye by: determining from the eye information a predicted anatomical feature when the eye is aligned for docking the patient interface onto the eye; detecting from the images an actual anatomical feature; and comparing the predicted anatomical feature with the actual anatomical feature to detect misalignment. The anatomical feature may be a pupil, an iris, a blood vessel, and/or a corneal vertex. The computer may determine the predicted anatomical feature from the eye information by: calculating the predicted anatomical feature for when an eye axis of the eye is horizontal from data gathered when the eye axis is vertical; calculating the predicted anatomical feature for when the eye is under lower intensity light from data gathered when the eye was under higher intensity light; and/or calculating the predicted anatomical feature for when the eye is in contact with the patient interface from data gathered when the eye was free from contact with the patient interface. The ophthalmic laser surgical system includes illuminators that illuminate the eye to yield reference reflections. The computer analyzes the reference reflections to determine the actual corneal surface position. The computer compares the predicted corneal surface position with the actual anterior surface shape by comparing a predicted vertex of the predicted corneal surface position to an actual vertex of the actual anterior surface shape. The computer compares the predicted corneal surface position with the actual anterior surface shape by comparing a predicted tilt of the predicted corneal surface position with an actual tilt of the actual anterior surface shape. The computer calculates an updated predicted corneal surface position after a change to the eye, and compares the updated predicted corneal surface position with the actual anterior surface shape to detect misalignment. The change to the eye may be: a suction portion of the patient interface is placed onto the eye; a contact portion of the patient interface is placed onto the eye; or the contact portion compresses the eye. The computer tracks movement of the eye according to the images. The computer, after docking, determines a distance to an iris of the eye and checks alignment according to the distance. The computer, after docking, determines a tilt of the eye and calculates a probability of suction loss according to the tilt. The computer, after docking, checks an alignment of the eye and calculates an adjustment to compensate for a misalignment of the eye.

In certain embodiments, an ophthalmic laser surgical system for treating an eye includes a laser device, illuminators, one or more cameras, and a computer. The eye has anatomical features, including the cornea with the anterior corneal surface. The laser device, with the device coordinate system, directs a laser beam towards the eye. The illuminators illuminate the eye to yield reference reflections. A camera generates images of the eye depicting the reference reflections and the anatomical features. The computer facilitates docking a patient interface onto the eye by accessing eye information describing the eye. The eye information comprises an eye model describing the anatomical features of the eye. The computer determines from the eye model the predicted corneal surface position when the eye is aligned to dock the patient interface onto the eye. The computer determines from the reference reflections the actual corneal surface position prior to docking the patient interface onto the eye, and compares the predicted corneal surface position with the actual corneal surface position to detect misalignment.

Embodiments may include none, one, some, or all of the following features: The illuminators include a central illuminator that provides a central illumination beam substantially aligned with a z-axis of the device coordinate system to yield a central reference reflection. The illuminators include a ring illumination system that provides one or more ring illumination beams substantially centered about with a z-axis of the device coordinate system to yield ring reference reflections. The computer determines the actual corneal surface position prior to docking the patient interface onto the eye by determining the actual corneal surface position according to the position of the reference reflections. The computer determines the actual corneal surface position prior to docking the patient interface onto the eye by determining the actual corneal surface position according to the shape of the reference reflections.

DESCRIPTION OF EXAMPLE EMBODIMENTS

Figure 1:
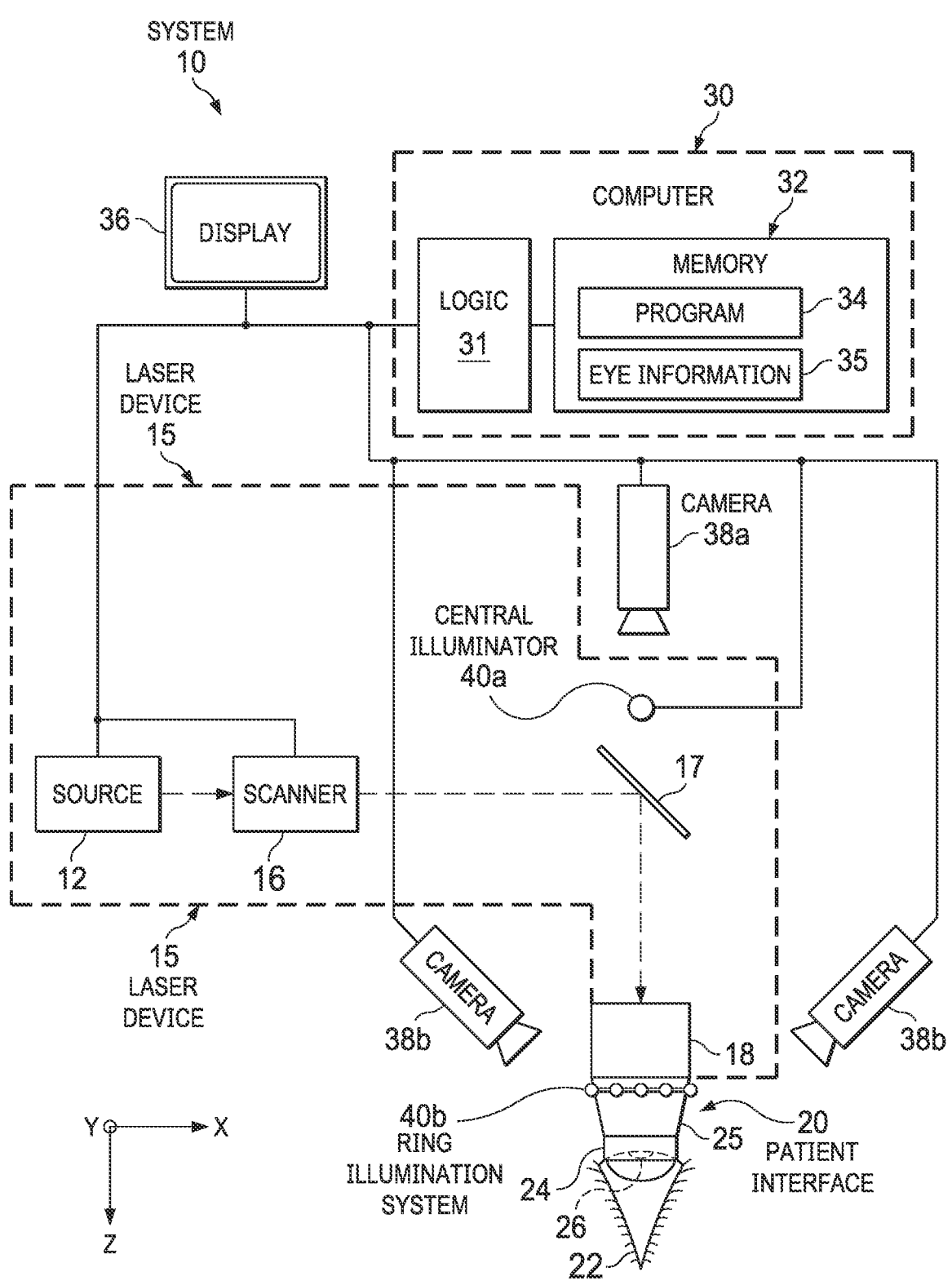
FIG. 1 illustrates an example of an ophthalmic surgical system configured to facilitate docking of an eye, according to certain embodiments.

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

To direct laser pulses precisely towards specific locations of an eye, the eye must be accurately docked to the laser system. Typically, a patient fixates on a fixation target for docking, but sometimes a patient cannot reliably fixate. Moreover, the eye may shift during docking.

To address these issues, embodiments described herein use diagnostic information, information captured during docking, and/or information calculated from the diagnostic and/or captured information to optimize the docking process. For example, a computer may use diagnostic information to predict the position of the anterior corneal surface when the eye is optimally aligned for docking. From images captured during the docking process, the computer may determine the actual position of the corneal surface and then compare the actual position with the predicted position to detect misalignment. The system may provide notification of and/or compensate for the misalignment in order to facilitate docking.

1. Example System

FIG. 1 illustrates an example of an ophthalmic surgical system 10 configured to facilitate docking of an eye 22, according to certain embodiments. Ophthalmic surgical system 10 may perform any suitable surgical procedure, such as corneal refractive surgery (e.g., small incision lenticule extraction (SMILE) or laser-assisted stromal in-situ keratomileusis (LASIK)) or other ophthalmic laser surgery. System 10 performs the surgical procedure according to a treatment pattern, which describes the target locations of the laser pulses on eye 22. To correctly perform the procedure, the treatment pattern must be properly aligned on eye 22. For the pattern to be properly aligned, the patient interface must be properly docked onto eye 22.

To describe the alignment between eye 22 and the patient interface, examples of a coordinate system for system 10 ("device coordinate system") and a coordinate system for eye 22 ("eye coordinate system") are provided. As an example, the z-axis of the device coordinate system may be a line that is substantially aligned with a central axis of a component of system 10, e.g., an axis of the laser device, laser beam delivery optics, and/or patient interface. The z-axis defines orthogonal xy-planes and may intersect the xy-origin $(x, y)=(0, 0)$ of the xy-planes. An xy-plane may correspond to an enface plane of eye 22, e.g., the iris plane of eye 22.

Turning to the eye coordinate system, eye 22 has eye features, including anatomical and geometrical features. Anatomical features include, e.g., the cornea, iris, pupil, and scleral blood vessels. These features may be imaged to determine if an xy-plane of system 10 is aligned with an enface plane of the eye. If the planes are not aligned, the xy-plane may be off-centered and/or rotated relative to eye 22. Geometrical features include an eye axis (e.g., optical or visual axis) and a central point (e.g., corneal vertex or pupil center). In certain embodiments, the patient interface may be determined to be aligned with eye 22 if the z-axis is substantially aligned with the eye axis and/or substantially intersects with the central point of the eye.

In the illustrated example, system 10 includes a laser device 15, a patient interface 20, one or more cameras 38 (38a, 38b), illuminators 40 (40a, 40b), and a control computer 30, coupled as shown. Laser device 15 includes controllable components, such as a laser source 12, a scanner 16, one or more optical elements 17, and/or a focusing objective 18, controllable by a computer such as computer 30, coupled as shown. Patient interface 20 includes a suction portion (e.g., a suction ring 24) and a sleeve 25 (with a contact portion 26). Cameras 38 include an on-axis camera 38a and off-axis cameras 38b. Illuminators 40 include a central illuminator 40a and a ring illumination system 40b. Computer 30 includes logic 31, a memory 32 (which stores a computer program 34 and eye information 35), and a display 36, coupled as shown.

As an overview, laser device 15 directs laser pulses towards eye 22. Cameras 38 generate images of the features of eye 22. Computer 30 facilitates docking patient interface 20 onto eye 22. Computer 30 stores eye information 35 describing eye 22, such as an eye model describing the eye features. Prior to docking patient interface 20 onto the eye, computer 30 determines the predicted corneal surface position when eye 22 is aligned for docking from eye information 35, and then detects the actual corneal surface position from the images. Computer 30 compares the predicted surface position with the actual surface position to detect misalignment. In certain embodiments, computer 30 may further predict from the eye information what an anatomical feature looks like when the eye is aligned for docking, detect the actual anatomical feature from the images, and compare the predicted anatomical feature with the actual anatomical feature to detect misalignment.

Turning to the parts of system 10, laser device directs laser pulses towards eye 22. As an overview, laser source 12 generates a laser beam that has ultrashort pulses. Scanner 16 longitudinally and transversely directs the focal point of the laser beam. Objective 18 focuses the focal point towards specific locations of eye 22. In more detail, laser source 12 generates a laser beam with ultrashort pulses. An ultrashort pulse refers to a light pulse that has a duration that is less than a nanosecond, such as on the order of picoseconds, femtoseconds, or attoseconds. The laser beam may have any suitable wavelength, such as a wavelength in the range of 300 to 1500 nanometers (nm), e.g., a wavelength in the range of 300 to 650, 650 to 1050, 1050 to 1250, and/or 1250 to 1500 nm, such as 340 to 350 nm, e.g., 347 nm±1 nm. The focal point of the laser beam may create a laser-induced optical breakdown (LIOB) in tissue (e.g., the cornea) to yield a photodisruption in the tissue. The laser beam may be precisely focused to yield precise photodisruptions, which may reduce or avoid unnecessary destruction of other tissue.

Scanner 16 longitudinally and transversely directs the focal point of the laser beam. The longitudinal direction refers to the direction of the laser beam propagation, i.e., the z-direction. Scanner 16 may longitudinally direct the laser beam in any suitable manner. For example, scanner 16 may include a longitudinally adjustable lens, a lens of variable refractive power, or a deformable mirror that can control the z-position of the focal point. The transverse direction refers to directions orthogonal to the direction of beam propagation, i.e., the x- and y-directions. Scanner 16 may transversely direct the laser beam in any suitable manner. For example, scanner 16 may include a pair of galvanometrically-actuated scanner mirrors that can be tilted about mutually perpendicular axes. As another example, scanner 16 may include an electro-optical crystal that can electro-optically steer the laser beam.

One (or more) optical elements 17 direct the laser beam towards focusing objective 18. An optical element 17 can act on (e.g., transmit, reflect, refract, diffract, collimate, condition, shape, focus, modulate, and/or otherwise act on) a laser beam. Examples of optical elements include a lens, prism, mirror, diffractive optical element (DOE), holographic optical element (HOE), and spatial light modulator (SLM). In the example, optical element 17 is a mirror. Focusing objective 18 focuses the focal point of laser beam through the patient interface 20 towards a point of eye 22. In the example, focusing objective 18 is an objective lens, e.g., an f-theta objective.

Patient interface 20 is affixed to the cornea of eye 22 to couple eye 22 to laser device 15. Sleeve 25 detachably couples to laser device 15, and suction ring 24 applies suction that couples sleeve 25 to eye 22. Sleeve 25 may be translucent or transparent to the laser beam and has a contact portion 26 that interfaces with the cornea. Contact portion 26 may have any suitable shape, e.g., planar or concave.

An illuminator 40 comprises a light source (e.g., a lamp or LED) or an array of light sources that provides light to illuminate eye 22. The light may yield reference reflections (e.g., light reflections or Purkinje reflections of higher order) that can be used to determine the location, position, and/or movement of eye 22. Examples of illuminators 40 include a central illuminator 40a (e.g., a fixation target) and a ring illumination system 40b. Central illuminator 40a may provide an illumination beam substantially aligned with the z-axis of the device coordinate system to yield a central reference reflection. In an example, the central reference reflection may be placed at a central point of the eye to optimally align the eye. Ring illumination system 40b may comprise, e.g., an annular illuminator or a plurality of spatially separated illuminators arranged in an annular pattern. Ring illumination system 40b provides one or more ring illumination beams centered about the z-axis of the device coordinate system to yield a ring of reference reflections that are centered about the z-axis of the device coordinate system. In an example, the ring of reference reflections may be substantially centered about the central point of the eye or aligned with the iris to optimally align the eye.

In certain embodiments, computer 30 may coordinate the illumination such that illumination from different illuminators 40 does not interact and degrade image quality. For example, computer 30 makes the illumination from one illuminator brighter than the illumination from another illuminator (e.g., turns on the illumination from one illuminator while turning off the illumination from the other). The coordination may involve synchronizing the illumination with the image capture process of cameras 38. For example, the illumination from one illuminator 40 is made brighter (e.g., turned on) when a camera 38 captures images.

Cameras 38 (38a, 38b) include any suitable camera that captures and generates images of eye 22, which may show eye features and/or reference reflections from illuminators 40. A camera 38 may include any suitable feature, such as an autofocus feature that can be used to determine the z-position of an eye feature. The autofocus focuses on a feature (e.g., the iris) and provides the z-position of the feature.

In the illustrated example, cameras 38 include an on-axis camera 38a and off-axis cameras 38b. On-axis camera 38a is substantially aligned with the z-axis of the device coordinate system to capture enface images of eye 22. On-axis camera 38a may perform any suitable function. For example, on-axis camera 38a can be used to determine if the patient interface is aligned in the xy-plane with eye 22, e.g., if the central point of the patient interface is aligned with the central point of eye 22. As another example, on-axis camera 38a can be used to determine corneal tilt. The autofocus feature determines the position of the iris plane relative to the patient interface to check if the iris plane is tilted relative to the interface. In the example, the autofocus feature may track movement of the iris towards the patient interface during docking to check for corneal tilt. As another example, on-axis camera 38a and computer 30 operate as an eye tracker that tracks the past, current, and/or predicted locations of eye features.

An off-axis camera 38b is not aligned with the z-axis of the device coordinate system, but positioned at an angle (greater than, e.g., 5 or 10 degrees) to the z-axis. Certain embodiments include multiple off-axis cameras 38b, such as stereoscopic cameras 38b. In the embodiments, off-axis cameras 38b capture images of eye features and/or reference reflections from different angles. The off-axis images may show, e.g., the corneal vertex.

Computer 30 facilitates and optimizes the docking process. In general, computer 30 determines the location, shape, and/or arrangement of eye features (e.g., the iris, corneal vertex, and/or pupil) and/or reference reflections when the patient interface is properly aligned with the eye, and predicts the proper location, shape, and/or arrangement of the eye features and/or reference reflections during the docking process (e.g., when the suction ring touches and applies suction to the eye, when the contact surface touches and compresses the eye). During docking, computer 30 analyzes images to determine the actual location, shape, and/or arrangement of eye features and/or reference reflections. Computer 30 then compares the actual location, shape, and/or arrangement with the predicted location, shape, and/or arrangement to detect misalignment. Computer 30 may use an eye model that describes features (e.g., refractive surfaces of the eye) of the eye and allows computer 30 to calculate the predicted and/or actual location, shape, and/or arrangement. The eye model may be adjusted in response to information captured during the docking process. In certain embodiments, computer 30 may display graphical overlays on an image of the eye that indicate where the patient interface should be placed onto eye for optimal alignment. For example, an overlay may indicate where a suction ring should be placed for optimal alignment.

Turning to the memory 32, computer 30 uses eye information 35, which includes diagnostic information, information captured during docking, and/or information calculated from the diagnostic and/or captured information to facilitate and/or optimize the docking process. Eye information 35 may include measurements and/or images of features of the eye, as well as information calculated from the measurements and/or images. Diagnostic information may be measured or determined prior to the procedure and/or during the procedure by a separate diagnostic device and/or by a diagnostic feature of the system 10.

Examples of diagnostic information include: tomography of the anterior segment (e.g., topography of the anterior and/or posterior corneal surfaces and pachymetry map of the cornea, iris, and/or lens); aberrometry wavefront map; eye dimensions (e.g., anterior chamber depth and axial length);

eye feature location, position, and/or movement (e.g., iris position and distance relative to corneal surface(s), pupil center distance relative to eye vertex, and pupil center shift); eye model of the eye; and eye feature images (e.g., images of the pupil (including pupil border structures), iris, and/or scleral blood vessels). Examples of information captured during docking may include: reference reflections (e.g., reflections of light from an illuminator(s)); eye feature images (such as described above); and eye tracker information (e.g., past, current, and/or predicted location, movement, and/or position of eye features).

Computer 30 may predict optimal eye alignment in any suitable manner. For example, an image of an eye feature (e.g., the iris or pupil) may be used to determine the location of an optimally aligned patient interface (e.g., centered with the iris or pupil). As another example, the shape of the anterior corneal surface may be used to predict the optimal arrangement of reference reflections, e.g., a central reference reflection should be at the eye's central point, or a ring of reference reflections should be centered about the central point.

As another example, mechanical properties of corneal tissue and eye information gathered when the eye is free from the patient interface may be used to predict eye information describing the eye compressed by the patient interface. As another example, eye information gathered when the eye is positioned with a vertical eye axis may be used to predict eye information for when the eye is positioned with a horizontal eye axis. As another example, eye information gathered when the eye is under higher intensity light may be used to predict eye information for when the eye is under lower intensity light.

Computer 30 may determine the actual eye alignment or other feature in any suitable manner. In general, computer 30 analyzes images of eye features and/or reference reflections to determine the actual eye alignment. For example, the shape of the anterior corneal surface and the arrangement of reference reflections (e.g., central and/or ring reflections) may be used to determine the location of the vertex of the eye and/or corneal tilt. As another example, the curvature of the eye and properties of the reflection may be used to determine the z-distance to the eye. As another example, the elongation of circular ring reflections may be used to determine the corneal tilt. As another example, the pupil/iris location and iris-to-interface distance may be used to calculate the corneal tilt. As another example, variation information of lateral water shift diameter and variation of iris-to-interface distance may be used to calculate the probability of suction loss.

2. Examples of Detecting Misalignment

Figure 2:
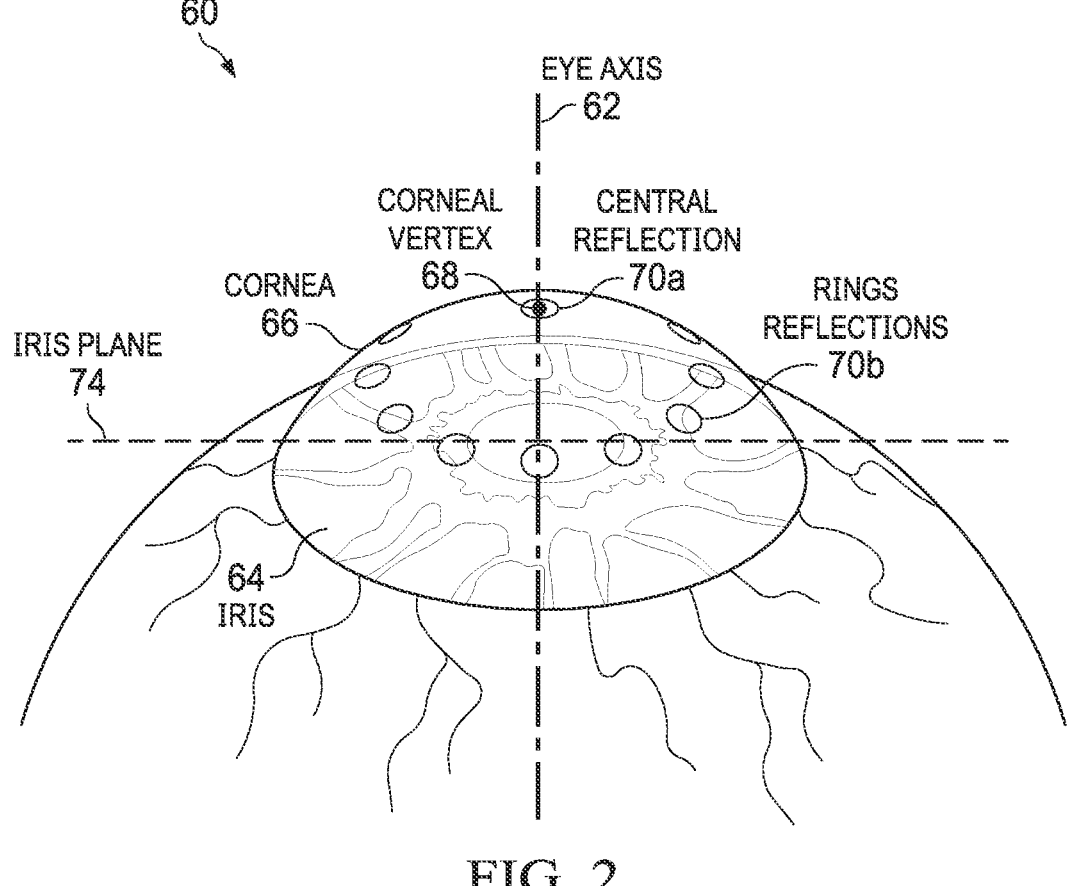
FIG. 2 is a diagram illustrating an example of how the system of FIG. 1 may use reference reflections to check for docking misalignment, according to certain embodiments.

FIG. 2 is a diagram 60 illustrating an example of how system 10 may use reference reflections to check for docking misalignment, according to certain embodiments. Diagram 60 shows an eye with an eye axis 62, an iris 64 defining an iris plane 74, and a cornea 66 with a corneal vertex 68. Reference reflections 70, such as central reflection 70a and ring reflections 70b, appear on the eye. The location, position, and/or arrangement of reference reflections 70 may indicate the alignment of the eye relative to system 10. For example, central reference reflection 70a may be placed at vertex 68 and/or ring reflections 70b may be centered about vertex 68 or aligned with iris 64 to optimally align the eye.

2.1 Off-Centered Eye. In certain embodiments, eye 22 may be defined to be centered if the origin (x, y)=(0, 0) of the device coordinate system is aligned with the central point (e.g., pupil center or corneal vertex) of eye 22. An acceptable tolerance limit may have a value in the range +/−50 to +/−500 micrometers, e.g., +/−100 micrometers. Centration may be determined in any suitable manner. For example, an on-axis camera images eye features (e.g., the central point) and/or reference reflections (e.g., central reflection 70a and/or ring reflections 70b). Computer 30 analyzes the images to determine if eye 22 is centered, e.g., determine if central reflection 70a and/or ring reflections 70b are centered with the central point of eye 22. As another example, multiple off-axis cameras image eye features (e.g., the corneal surface such as the corneal vertex) and/or reference reflections from different angles. Computer 30 analyzes the images to determine if eye 22 is centered, e.g., determine if central reflection 70a and/or ring reflections 70b are centered with the corneal vertex of eye 22.

In certain embodiments, computer 30 determines how the location of the central point (e.g., the pupil center) shifts under different conditions, e.g., vertical versus horizontal eye axis, darker illumination versus lighter illumination, or in contact with the patient interface versus free from contact. Computer 30 may compensate for the central point shift to properly align the patient interface. For example, computer 30 may determine how the central point shifts before contact with and when in contact with the patient interface, and may align the patient interface with where the central point should be when in contact with the patient interface.

2.2 Rotated Eye. In certain embodiments, eye 22 may be defined to be rotationally aligned if an xy-plane of device coordinate system is rotationally aligned with a corresponding enface plane of eye 22. For example, graphical features of the xy-plane (e.g., a reticle) may be defined to correspond to anatomical features (e.g., iris features or blood vessels) imaged at the enface plane of eye 22. An acceptable tolerance limit may have a value in the range +/−1 to +/−10 degrees, e.g., +/−3 degrees. Rotation may be determined in any suitable manner. For example, an on-axis camera images eye features (e.g., iris features or blood vessels) and/or reference reflections to determine if eye 22 is rotationally aligned. As another example, multiple off-axis cameras image of eye features (e.g., corneal surface) and/or reference reflections from different angles to determine if eye 22 is rotationally aligned. Similar to as described in Section 2.1 relative to centration, system 10 may determine how features of eye 22 shift rotationally under different conditions and may compensate for rotational shift to properly align the patient interface.

2.3 Tilted Eye. In certain embodiments, eye 22 may be defined to be angularly aligned if the z-axis of the device coordinate system is aligned with the eye axis of eye 22. Otherwise, eye 22 may be regarded as tilted. An acceptable tolerance limit may have a value in the range +/−0.5 to +/−5 degrees, e.g., +/−1 degree. Tilt may be determined in any suitable manner. For example, multiple off-axis cameras image eye features (e.g., the corneal surface) and/or reference reflections from different angles to determine the tilt of corneal anterior surface. As another example, an on-axis camera may be used to determine corneal tilt. In the example, the autofocus feature of the camera determines the position of iris plane 74 relative to the patient interface. If iris plane 74 is not parallel to the contact portion of the patient interface, eye 22 may be tilted relative to the interface.

3. Example Method

Figure 3:
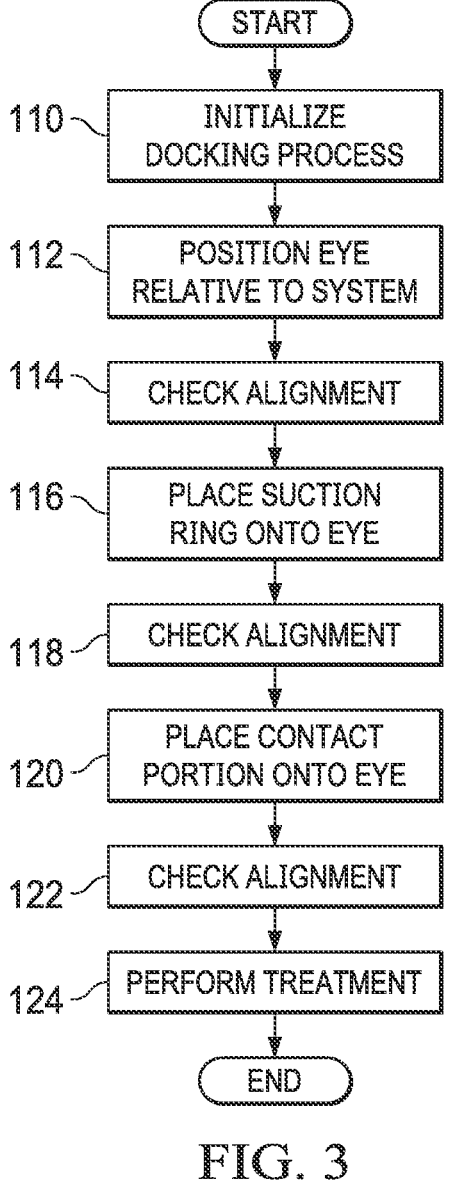
FIG. 3 illustrates an example of a method for docking an eye that may be used by the system of FIG. 1, according to certain embodiments.

FIG. 3 illustrates an example of a method for docking an eye that may be used with system 10 of FIG. 1, according to certain embodiments. The method checks for misalignment between patient interface 20 and eye 22 by comparing a predicted location, shape, and/or arrangement of an eye feature and/or reference reflection with the actual location, shape, and/or arrangement. The method may check for misalignment periodically and/or after a change to the eye, e.g., a suction ring is placed onto the eye, the suction ring is adjusted (e.g., removed and replaced), a contact portion is placed onto the eye, and/or the contact portion compresses the eye. If a misalignment exceeds an acceptable tolerance at any point of the method, system 10 may automatically correct the misalignment and/or provide a notification of the misalignment.

The method starts at step 110, where the docking process is initialized. In certain embodiments, a computer of the system accesses a treatment pattern and eye information. As described above, the eye information includes an eye model, diagnostic information, information captured during the docking process, and/or information calculated from the diagnostic and/or captured information to facilitate and/or optimize the docking process.

The eye is positioned relative to the system at step 112. In certain embodiments, the patient fixates on a central illuminator, e.g., a fixation light. The alignment is checked at step 114. For example, the system may check for offset, rotation, and/or corneal tilt, as described with reference to FIG. 2. On-axis and/or off-axis cameras may image eye features and/or reference reflections to determine the actual locations of eye features, as described with reference to FIG. 2. For example, an on-axis camera may image the pupil to determine the pupil center, and off-axis cameras may image reference reflections to determine the location of the corneal vertex.

The suction ring is placed onto the eye at step 116. In certain embodiments, the user places the suction ring onto the eye, which may change the anterior corneal surface and reference reflections. From the eye model, the system predicts the changes, e.g., how the pupil center shifts or how the corneal surface changes, in response to the suction ring placement.

The alignment is checked at step 118. The system checks the alignment of the suction ring from images of the eye features and/or reference reflections. For example, a central point of the ring may be placed substantially at a central point of the eye. In certain embodiments, the system switches from off-axis cameras to an on-axis camera above the eye. The on-axis camera may be used to check for decentration, rotation, and/or tilt as described with reference to FIG. 2.

The contact portion is placed onto the eye at step 120. The contact portion typically touches the cornea first at the vertex. As the contact portion presses the eye, eye features and reference reflections may change and/or disappear. For example, if the contact portion is planar, the corneal vertex may disappear, and the pupil shape may change, which shifts the pupil center. In certain embodiments, the system predicts the changes by estimating from the eye model and position of the suction ring how the corneal tissue moves during compression.

Alignment is checked at step 122. The system analyzes images of the eye features and/or reference reflections and other information to check the alignment. For example, the camera autofocus provides the z-distance of the contact portion relative to the iris plane to check for tilt. This information, along with lateral water shift information, may also be used to calculate the probability of suction loss from the suction ring. In certain embodiments, the system can use information obtained during the docking process to compensate for any misalignment during treatment, e.g., recenter the treatment pattern or adjust the treatment profile (e.g., depth and/or energy settings). The treatment is performed at step 124. The method then ends.

A component (such as computer 30) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface is a type of interface that a user can utilize to communicate with (e.g., send input to and/or receive output from) a computer. Examples of user interfaces include a display, Graphical User Interface (GUI), touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by an electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. An ophthalmic laser surgical system for treating an eye, comprising:

a laser device configured to direct a laser beam towards the eye, the eye having a plurality of anatomical features, the anatomical features comprising a cornea with an anterior corneal surface;

one or more cameras, each camera configured to generate a plurality of images of the anatomical features of the eye, the images depicting the anterior corneal surface; and a computer configured to facilitate docking a patient interface onto the eye by:

accessing eye information describing the eye, the eye information comprising an eye model describing the anatomical features of the eye;

determining from the eye model a predicted corneal vertex of a predicted corneal surface position when the eye is aligned to dock the patient interface onto the eye;

detecting from the images an actual corneal vertex of an actual corneal surface position prior to docking the patient interface onto the eye; and comparing the predicted corneal vertex of the predicted corneal surface position with the actual corneal vertex of the actual corneal surface position to detect misalignment.

2. The ophthalmic laser surgical system of claim 1, the computer further configured to facilitate docking the patient interface onto the eye by:

determining from the eye information a predicted anatomical feature when the eye is aligned for docking the patient interface onto the eye;

detecting from the images an actual anatomical feature; and comparing the predicted anatomical feature with the actual anatomical feature to detect misalignment.

3. The ophthalmic laser surgical system of claim 2, the predicted anatomical feature and the actual anatomical feature comprising a feature of the following: a pupil, an iris, or a blood vessel.

4. The ophthalmic laser surgical system of claim 2, the computer configured to determine the predicted anatomical feature from the eye information by:

calculating the predicted anatomical feature for when an eye axis of the eye is horizontal from data gathered when the eye axis is vertical.

5. The ophthalmic laser surgical system of claim 2, the computer configured to determine the predicted anatomical feature from the eye information by:

calculating the predicted anatomical feature for when the eye is under lower intensity light from data gathered when the eye was under higher intensity light.

6. The ophthalmic laser surgical system of claim 2, the computer configured to determine the predicted anatomical feature from the eye information by:

calculating the predicted anatomical feature for when the eye is in contact with the patient interface from data gathered when the eye was free from contact with the patient interface.

7. The ophthalmic laser surgical system of claim 1:

further comprising a plurality of illuminators configured to illuminate the eye to yield a plurality of reference reflections; and the computer configured to analyze the reference reflections to determine the actual corneal surface position.

8. The ophthalmic laser surgical system of claim 1, the computer configured to compare the predicted corneal vertex of the predicted corneal surface position with the actual corneal vertex of the actual corneal surface position by:

comparing a predicted tilt of the predicted corneal surface position with an actual tilt of the actual corneal surface position.

9. The ophthalmic laser surgical system of claim 1, the computer further configured to:

calculate an updated predicted corneal surface position after a change to the eye; and compare the updated predicted corneal surface position with the actual corneal surface position to detect misalignment.

10. The ophthalmic laser surgical system of claim 9, the change to the eye comprising one of the following:

a suction portion of the patient interface is placed onto the eye;

a contact portion of the patient interface is placed onto the eye; and the contact portion compresses the eye.

11. The ophthalmic laser surgical system of claim 1, the computer further configured to:

track movement of the eye according to the plurality of images.

12. The ophthalmic laser surgical system of claim 1, the computer further configured to:

after docking, determine a distance to an iris of the eye; and check alignment according to the distance.

13. The ophthalmic laser surgical system of claim 1, the computer further configured to:

after docking, determine a tilt of the eye; and calculate a probability of suction loss according to the tilt.

14. The ophthalmic laser surgical system of claim 1, the computer further configured to:

after docking, check an alignment of the eye; and calculate an adjustment to compensate for a misalignment of the eye.

* * * * *